(12) United States Patent
Casey et al.

(10) Patent No.: US 9,517,089 B1
(45) Date of Patent: Dec. 13, 2016

(54) BONE ANCHOR WITH OFFSET ROD CONNECTOR

(71) Applicant: NuVasive, Inc., San Diego, CA (US)

(72) Inventors: Niall Casey, San Diego, CA (US); Daniel Zatta, San Diego, CA (US); Seth Gustine, Encinitas, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/510,107

(22) Filed: Oct. 8, 2014

Related U.S. Application Data

(60) Provisional application No. 61/888,480, filed on Oct. 8, 2013.

(51) Int. Cl.
*A61B 17/70* (2006.01)

(52) U.S. Cl.
CPC ....... *A61B 17/7035* (2013.01); *A61B 17/7041* (2013.01)

(58) Field of Classification Search
CPC ................. A61B 17/7035; A61B 17/7041
USPC ....... 606/246, 264–272, 278, 301, 305, 308; 411/393
See application file for complete search history.

(56) References Cited

U.S. PATENT DOCUMENTS

| | | |
|---|---|---|
| 3,196,876 A | 7/1965 | Miller |
| 3,741,205 A | 6/1973 | Markolf |
| 3,788,318 A | 1/1974 | Kim |
| 3,997,138 A | 12/1976 | Crock |
| 4,047,524 A | 9/1977 | Hall |
| 4,289,123 A | 9/1981 | Dunn |
| 4,545,374 A | 10/1985 | Jacobson |
| 4,611,581 A | 9/1986 | Steffee |
| 4,620,533 A | 11/1986 | Mears |
| 4,648,388 A | 3/1987 | Steffee |
| 4,653,481 A | 3/1987 | Howland |
| 4,773,402 A | 9/1988 | Asher |
| 5,002,542 A | 3/1991 | Frigg |
| 5,024,213 A | 6/1991 | Asher |
| 5,047,029 A | 9/1991 | Aebi et al. |
| 5,074,864 A | 12/1991 | Cozad |
| 5,085,660 A | 2/1992 | Lin |
| 5,108,395 A | 4/1992 | Laurain |
| 5,129,899 A | 7/1992 | Small |
| 5,137,509 A | 8/1992 | Freitas |
| 5,147,360 A | 9/1992 | Dubousset |
| 5,147,361 A | 9/1992 | Ojima |

(Continued)

FOREIGN PATENT DOCUMENTS

| | | |
|---|---|---|
| CA | 2045502 | 5/1991 |
| CN | 2162921 Y | 4/1994 |

(Continued)

*Primary Examiner* — Pedro Philogene
*Assistant Examiner* — David C Comstock
(74) *Attorney, Agent, or Firm* — Nicholas J. Landau; Bradley Arant Boult Cummings LLP

(57) ABSTRACT

This disclosure describes example an surgical fixation anchor and methods for implanting the surgical fixation anchor on the spine as part of a spinal fixation construct. The surgical fixation anchor can be coupled to a spinal rod. The coupling between the spinal rod and the anchor can be offset from an axis of the anchor. The position and orientation of the coupling to the spinal rod can also be transnationally and rotationally adjusted relative to the anchor to facilitate the coupling and/or to optimize space usage adjacent to the fixation construct.

18 Claims, 6 Drawing Sheets

(56) References Cited

U.S. PATENT DOCUMENTS

| | | | |
|---|---|---|---|
| 5,152,303 A | 10/1992 | Allen |
| 5,158,543 A | 10/1992 | Lazarus |
| 5,196,013 A | 3/1993 | Harms et al. |
| 5,209,752 A | 5/1993 | Ashman et al. |
| 5,242,427 A | 9/1993 | Bilweis |
| 5,261,909 A | 11/1993 | Sutterlin |
| 5,306,275 A | 4/1994 | Bryan |
| 5,324,290 A | 6/1994 | Zdeblick |
| 5,330,473 A | 7/1994 | Howland |
| 5,364,399 A | 11/1994 | Lowery |
| 5,368,594 A | 11/1994 | Martin |
| 5,380,323 A | 1/1995 | Howland |
| 5,380,324 A | 1/1995 | Muller |
| 5,380,325 A | 1/1995 | Lahille |
| 5,401,247 A | 3/1995 | Yoon |
| 5,445,617 A | 8/1995 | Yoon |
| 5,476,467 A | 12/1995 | Benoist |
| 5,520,690 A | 5/1996 | Errico |
| 5,549,608 A | 8/1996 | Errico |
| 5,569,289 A | 10/1996 | Yoon |
| 5,573,511 A | 11/1996 | Yoon |
| 5,575,791 A | 11/1996 | Lin |
| 5,584,831 A | 12/1996 | McKay |
| 5,603,714 A | 2/1997 | Kaneda |
| 5,613,968 A | 3/1997 | Lin |
| 5,620,443 A | 4/1997 | Gertzbein |
| 5,662,652 A | 9/1997 | Schafer |
| 5,662,653 A | 9/1997 | Songer |
| 5,665,072 A | 9/1997 | Yoon |
| 5,667,509 A | 9/1997 | Westin |
| 5,672,176 A | 9/1997 | Harms |
| 5,681,312 A | 10/1997 | Yuan |
| 5,690,629 A | 11/1997 | Asher |
| 5,697,947 A | 12/1997 | Wolf |
| 5,702,395 A | 12/1997 | Hopf |
| 5,704,936 A | 1/1998 | Mazel |
| 5,713,898 A | 2/1998 | Stucker |
| 5,713,900 A | 2/1998 | Benzel |
| 5,728,127 A | 3/1998 | Asher |
| 5,741,255 A | 4/1998 | Krag et al. |
| 5,766,254 A | 6/1998 | Gelbard |
| 5,772,678 A | 6/1998 | Thomason |
| 5,800,435 A | 9/1998 | Errico |
| 5,842,478 A | 12/1998 | Benderev |
| 5,882,350 A | 3/1999 | Ralph |
| 5,899,902 A | 5/1999 | Brown |
| 5,899,904 A | 5/1999 | Errico |
| 5,899,905 A | 5/1999 | Errico |
| 5,925,047 A | 7/1999 | Errico |
| 5,928,233 A | 7/1999 | Apfelbaum |
| 5,928,243 A | 7/1999 | Guyer |
| 5,938,663 A | 8/1999 | Petreto |
| 5,947,969 A | 9/1999 | Errico |
| 5,976,135 A | 11/1999 | Sherman |
| 5,976,146 A | 11/1999 | Ogawa |
| 6,004,322 A | 12/1999 | Bernstein |
| 6,033,420 A | 3/2000 | Hahnen |
| 6,063,090 A | 5/2000 | Schlapfer |
| 6,066,140 A | 5/2000 | Gertzbein |
| 6,083,224 A | 7/2000 | Gertzbein |
| 6,083,226 A | 7/2000 | Fiz |
| 6,090,110 A | 7/2000 | Metz-Stavenhagen |
| 6,106,526 A | 8/2000 | Harms et al. |
| 6,117,135 A | 9/2000 | Schläpfer |
| 6,123,706 A | 9/2000 | Lange |
| 6,126,660 A | 10/2000 | Dietz |
| 6,126,691 A | 10/2000 | Kasra |
| 6,132,431 A | 10/2000 | Nilsson |
| 6,136,000 A | 10/2000 | Louis |
| 6,136,002 A | 10/2000 | Shih |
| 6,152,927 A | 11/2000 | Farris |
| 6,176,861 B1 | 1/2001 | Brumfield |
| 6,179,838 B1 | 1/2001 | Fiz |
| 6,183,473 B1 | 2/2001 | Ashman |
| 6,187,005 B1 | 2/2001 | Brace |
| 6,206,879 B1 | 3/2001 | Marnay |
| 6,210,413 B1 | 4/2001 | Justis et al. |
| 6,214,006 B1 | 4/2001 | Metz-Stavenhagen |
| 6,224,602 B1 | 5/2001 | Hayes |
| 6,231,575 B1* | 5/2001 | Krag .................. 606/264 |
| 6,234,705 B1 | 5/2001 | Troxell |
| 6,248,105 B1 | 6/2001 | Hess |
| 6,254,603 B1 | 7/2001 | Gertzbein |
| 6,261,265 B1 | 7/2001 | Mosseri |
| 6,261,288 B1 | 7/2001 | Jackson |
| 6,280,445 B1 | 8/2001 | Johnson |
| 6,283,967 B1 | 9/2001 | Kumar |
| 6,287,308 B1 | 9/2001 | Drewry |
| 6,296,643 B1 | 10/2001 | Hopf |
| 6,299,613 B1 | 10/2001 | Ogilvie |
| 6,379,357 B1 | 4/2002 | Bernstein |
| 6,395,007 B1 | 5/2002 | Bhatnagar |
| 6,402,749 B1 | 6/2002 | Ashman |
| 6,416,515 B1 | 7/2002 | Wagner |
| 6,447,483 B1 | 9/2002 | Steube |
| 6,471,703 B1 | 10/2002 | Ashman |
| 6,471,704 B2 | 10/2002 | Gertzbein |
| 6,471,706 B1 | 10/2002 | Schumacher |
| 6,482,207 B1 | 11/2002 | Errico |
| 6,488,682 B2 | 12/2002 | Kikuchi |
| 6,520,962 B1 | 2/2003 | Taylor et al. |
| 6,524,311 B2 | 2/2003 | Gaines |
| 6,524,315 B1 | 2/2003 | Selvitelli |
| 6,533,786 B1 | 3/2003 | Needham |
| 6,533,787 B1 | 3/2003 | Lenke |
| 6,537,276 B2 | 3/2003 | Metz-Stavenhagen |
| 6,551,320 B2 | 4/2003 | Lieberman |
| 6,565,569 B1 | 5/2003 | Assaker |
| 6,569,164 B1 | 5/2003 | Assaker |
| 6,572,622 B1 | 6/2003 | Schäfer |
| 6,576,016 B1 | 6/2003 | Hochshuler |
| 6,585,740 B2 | 7/2003 | Schläpfer |
| 6,602,254 B2 | 8/2003 | Gertzbein |
| 6,616,669 B2 | 9/2003 | Ogilvie |
| 6,623,484 B2 | 9/2003 | Betz |
| 6,626,906 B1 | 9/2003 | Young |
| 6,641,564 B1 | 11/2003 | Kraus |
| 6,641,614 B1 | 11/2003 | Wagner |
| 6,645,207 B2 | 11/2003 | Dixon |
| 6,648,887 B2 | 11/2003 | Ashman |
| 6,652,525 B1 | 11/2003 | Assaker |
| 6,656,179 B1 | 12/2003 | Schaefer |
| 6,663,631 B2 | 12/2003 | Kuntz |
| 6,669,700 B1 | 12/2003 | Farris |
| 6,685,705 B1 | 2/2004 | Taylor |
| 6,702,817 B2 | 3/2004 | Beger |
| 6,706,044 B2 | 3/2004 | Kuslich |
| 6,746,450 B1 | 6/2004 | Wall |
| 6,749,612 B1 | 6/2004 | Conchy |
| 6,755,839 B2 | 6/2004 | Van Hoeck |
| 6,780,186 B2 | 8/2004 | Errico |
| 6,786,875 B2 | 9/2004 | Barker |
| 6,802,844 B2 | 10/2004 | Ferree |
| 6,858,029 B2 | 2/2005 | Yeh |
| 6,872,209 B2 | 3/2005 | Morrison |
| 6,881,215 B2 | 4/2005 | Assaker |
| 6,899,714 B2 | 5/2005 | Vaughan |
| 6,902,565 B2 | 6/2005 | Berger |
| 6,916,319 B2 | 7/2005 | Munting |
| 6,916,320 B2 | 7/2005 | Michelson |
| 6,945,972 B2* | 9/2005 | Frigg et al. .................. 606/256 |
| 6,945,975 B2 | 9/2005 | Dalton |
| 6,960,212 B2 | 11/2005 | Richelsoph |
| 6,969,390 B2 | 11/2005 | Michelson |
| 6,979,334 B2 | 12/2005 | Dalton |
| 7,001,387 B2 | 2/2006 | Farris |
| 7,001,396 B2 | 2/2006 | Glazier |
| 7,008,423 B2 | 3/2006 | Assaker |
| 7,022,085 B2 | 4/2006 | Cooke |
| 7,066,939 B2 | 6/2006 | Taylor |
| 7,083,622 B2 | 8/2006 | Simonson |
| 7,094,238 B2 | 8/2006 | Morrison |
| 7,115,129 B2 | 10/2006 | Heggeness |
| 7,137,984 B2 | 11/2006 | Michelson |

(56) References Cited

U.S. PATENT DOCUMENTS

| | | |
|---|---|---|
| 7,166,108 B2 | 1/2007 | Mazda |
| 7,172,600 B2 | 2/2007 | Beger |
| 7,172,612 B2 | 2/2007 | Ishikawa |
| 7,186,255 B2 * | 3/2007 | Baynham et al. ............ 606/266 |
| 7,211,087 B2 | 5/2007 | Young |
| 7,241,074 B2 | 7/2007 | Thomke |
| 7,250,054 B2 | 7/2007 | Allen |
| 7,252,670 B2 | 8/2007 | Morrison |
| 7,255,699 B2 | 8/2007 | Paul |
| 7,291,151 B2 | 11/2007 | Alvarez |
| 7,311,712 B2 | 12/2007 | Dalton |
| 7,344,537 B1 | 3/2008 | Mueller |
| 7,377,923 B2 | 5/2008 | Purcell |
| 7,455,684 B2 | 11/2008 | Gradel |
| 7,491,205 B1 | 2/2009 | Michelson |
| 7,507,248 B2 | 3/2009 | Beaurain |
| 7,559,929 B2 | 7/2009 | Denti |
| 7,572,277 B2 | 8/2009 | Roussouly |
| 7,585,299 B2 | 9/2009 | Rezach |
| 7,601,167 B2 | 10/2009 | Lieberman |
| 7,618,430 B2 | 11/2009 | Scheib |
| 7,621,914 B2 | 11/2009 | Ralph |
| 7,637,952 B2 | 12/2009 | Landry |
| 7,641,701 B2 | 1/2010 | Kirschman |
| 7,643,884 B2 | 1/2010 | Pond |
| 7,651,497 B2 | 1/2010 | Michelson |
| 7,658,739 B2 | 2/2010 | Shluzas |
| 7,658,754 B2 | 2/2010 | Zhang |
| 7,662,185 B2 | 2/2010 | Alfaro |
| 7,666,185 B2 | 2/2010 | Ryan |
| 7,678,113 B2 | 3/2010 | Melkent |
| 7,682,392 B2 | 3/2010 | Serhan |
| 7,699,874 B2 | 4/2010 | Young |
| 7,699,876 B2 | 4/2010 | Barry |
| 7,704,270 B2 | 4/2010 | de Coninck |
| 7,704,271 B2 | 4/2010 | Abdou |
| 7,717,938 B2 | 5/2010 | Kim |
| 7,722,645 B2 | 5/2010 | Bryan |
| 7,731,734 B2 | 6/2010 | Clement |
| 7,740,633 B2 | 6/2010 | Assell |
| 7,744,635 B2 * | 6/2010 | Sweeney et al. ............ 606/264 |
| 7,763,051 B2 | 7/2010 | Labrom |
| 7,763,054 B2 | 7/2010 | Clement |
| 7,789,895 B2 | 9/2010 | Heinz |
| 7,789,897 B2 | 9/2010 | Sanders |
| 7,789,900 B2 | 9/2010 | Levy |
| 7,803,174 B2 | 9/2010 | Denis |
| 7,806,912 B2 | 10/2010 | Lawton |
| 7,842,038 B2 | 11/2010 | Haddock |
| 7,862,593 B2 | 1/2011 | Clement |
| D633,208 S | 2/2011 | Murner |
| 7,883,510 B2 | 2/2011 | Kim |
| 7,883,531 B2 | 2/2011 | de Coninck |
| 7,892,260 B2 | 2/2011 | Mahoney |
| 7,942,902 B2 | 5/2011 | Schwab |
| 7,942,907 B2 | 5/2011 | Richelsoph |
| 7,959,654 B2 | 6/2011 | Mazda |
| RE42,545 E | 7/2011 | Ralph |
| 7,988,691 B2 | 8/2011 | Schulze |
| 7,993,380 B2 | 8/2011 | Hawkes |
| 8,007,520 B2 | 8/2011 | Metz-Stavenhagen |
| 8,029,546 B2 * | 10/2011 | Capote et al. ............... 606/257 |
| 8,034,082 B2 | 10/2011 | Lee |
| 8,034,085 B2 | 10/2011 | Slivka |
| 8,052,725 B2 | 11/2011 | Biedermann |
| 8,083,778 B2 | 12/2011 | Clement |
| 8,123,749 B2 | 2/2012 | Serhan |
| 8,131,346 B2 | 3/2012 | Chesbrough |
| 8,133,283 B2 | 3/2012 | Wilson |
| 8,147,527 B2 | 4/2012 | Hoffman |
| 8,162,988 B2 | 4/2012 | Delecrin |
| 8,167,899 B2 | 5/2012 | Justis |
| 8,197,516 B2 | 6/2012 | Biyani |
| 8,202,216 B2 | 6/2012 | Melkent |
| 8,206,291 B2 | 6/2012 | Fischvogt |
| D663,030 S | 7/2012 | Murner |
| 8,211,151 B2 | 7/2012 | Schwab |
| 8,211,152 B2 | 7/2012 | Snyder |
| 8,221,457 B2 | 7/2012 | Delecrin |
| 8,221,468 B2 | 7/2012 | Gaines |
| 8,231,659 B2 | 7/2012 | Zolotov |
| 8,241,285 B2 | 8/2012 | Mullaney |
| 8,262,626 B2 | 9/2012 | Levendusky |
| 8,262,710 B2 | 9/2012 | Freedman |
| 8,298,269 B2 | 10/2012 | Null et al. |
| 8,313,459 B2 | 11/2012 | Kiehne |
| 8,317,835 B2 | 11/2012 | Tornier |
| 8,323,318 B2 | 12/2012 | Baccelli |
| 8,323,319 B2 | 12/2012 | Mazda |
| 8,328,836 B2 | 12/2012 | Conlon |
| 8,337,527 B2 | 12/2012 | Hawkins |
| 8,361,130 B2 | 1/2013 | Daly |
| 8,382,804 B2 | 2/2013 | Thomke |
| 8,388,661 B2 | 3/2013 | Schlaepfer |
| 8,414,616 B2 | 4/2013 | Berrevoets |
| 8,430,916 B1 | 4/2013 | Winslow |
| D682,426 S | 5/2013 | Dominik |
| D683,461 S | 5/2013 | Murner |
| 8,435,267 B2 | 5/2013 | Chin |
| 8,454,658 B2 | 6/2013 | Lindner |
| 8,469,963 B2 | 6/2013 | Shoham |
| 8,470,000 B2 | 6/2013 | Trautwein |
| 8,506,598 B1 | 8/2013 | Tohmeh |
| 8,506,602 B2 | 8/2013 | Slivka |
| 8,518,087 B2 | 8/2013 | Lopez |
| 8,523,923 B2 | 9/2013 | Thomke |
| 8,568,456 B2 | 10/2013 | Black |
| 8,585,741 B2 | 11/2013 | Gabelberger |
| 2001/0001119 A1 | 5/2001 | Lombardo |
| 2001/0010000 A1 | 7/2001 | Gertzbein |
| 2002/0068940 A1 | 6/2002 | Gaines |
| 2002/0193795 A1 | 12/2002 | Gertzbein |
| 2003/0120275 A1 | 6/2003 | Lenke |
| 2003/0144665 A1 | 7/2003 | Munting |
| 2003/0171752 A1 | 9/2003 | Assaker |
| 2003/0187438 A1 | 10/2003 | Assaker |
| 2004/0138661 A1 | 7/2004 | Bailey |
| 2004/0147928 A1 | 7/2004 | Landry |
| 2004/0147929 A1 | 7/2004 | Biedermann |
| 2004/0162558 A1 | 8/2004 | Hegde |
| 2004/0236333 A1 | 11/2004 | Lin |
| 2004/0254574 A1 | 12/2004 | Morrison |
| 2004/0267262 A1 | 12/2004 | Link |
| 2005/0010215 A1 | 1/2005 | Delecrin |
| 2005/0038433 A1 | 2/2005 | Young |
| 2005/0154388 A1 | 7/2005 | Roussouly |
| 2005/0171537 A1 | 8/2005 | Mazel |
| 2005/0171538 A1 | 8/2005 | Sgier |
| 2005/0277920 A1 | 12/2005 | Slivka |
| 2006/0004359 A1 | 1/2006 | Kramer |
| 2006/0004360 A1 | 1/2006 | Kramer |
| 2006/0009766 A1 | 1/2006 | Lee |
| 2006/0036250 A1 | 2/2006 | Lange |
| 2006/0052811 A1 | 3/2006 | Blanco |
| 2006/0079892 A1 | 4/2006 | Roychowdhury |
| 2006/0079899 A1 | 4/2006 | Ritland |
| 2006/0116676 A1 | 6/2006 | Gradel |
| 2006/0167455 A1 | 7/2006 | Clement |
| 2006/0206114 A1 | 9/2006 | Ensign |
| 2006/0229606 A1 | 10/2006 | Clement |
| 2006/0229616 A1 | 10/2006 | Albert |
| 2006/0241601 A1 | 10/2006 | Trautwein |
| 2006/0253118 A1 | 11/2006 | Bailey |
| 2007/0049932 A1 | 3/2007 | Richelsoph |
| 2007/0078463 A1 | 4/2007 | Malandain |
| 2007/0118124 A1 | 5/2007 | Biedermann |
| 2007/0123860 A1 | 5/2007 | Francis |
| 2007/0162006 A1 | 7/2007 | Ritland |
| 2007/0233066 A1 | 10/2007 | Rezach |
| 2007/0255305 A1 | 11/2007 | McMichael |
| 2007/0270810 A1 | 11/2007 | Sanders |
| 2007/0270816 A1 | 11/2007 | Rezach |
| 2007/0270817 A1 | 11/2007 | Rezach |
| 2007/0270818 A1 | 11/2007 | Rezach |

(56) References Cited

U.S. PATENT DOCUMENTS

| | | |
|---|---|---|
| 2007/0282365 A1 | 12/2007 | Popov |
| 2007/0299459 A1 | 12/2007 | Way |
| 2008/0051780 A1* | 2/2008 | Vaidya et al. .......... 606/61 |
| 2008/0051821 A1 | 2/2008 | Gephart |
| 2008/0140124 A1 | 6/2008 | Jeon |
| 2008/0177323 A1 | 7/2008 | Null |
| 2008/0208257 A1 | 8/2008 | Matthys |
| 2008/0255617 A1 | 10/2008 | Cho |
| 2008/0262553 A1 | 10/2008 | Hawkins |
| 2008/0294203 A1 | 11/2008 | Kovach |
| 2008/0300630 A1 | 12/2008 | Bonnema |
| 2008/0306551 A1 | 12/2008 | Sanders |
| 2009/0099602 A1 | 4/2009 | Aflatoon |
| 2009/0131985 A1 | 5/2009 | Mazda |
| 2009/0138048 A1 | 5/2009 | Baccelli |
| 2009/0143738 A1 | 6/2009 | Hendriksen |
| 2009/0149857 A1 | 6/2009 | Culbert |
| 2009/0163942 A1 | 6/2009 | Cuevas |
| 2009/0182379 A1 | 7/2009 | Baccelli |
| 2009/0187217 A1 | 7/2009 | Weiman |
| 2009/0216242 A1 | 8/2009 | Riemer |
| 2009/0264926 A1 | 10/2009 | Taylor |
| 2009/0275970 A1 | 11/2009 | Leibowitz |
| 2009/0326585 A1 | 12/2009 | Baccelli |
| 2009/0326588 A1 | 12/2009 | Felix |
| 2010/0094346 A1 | 4/2010 | Matityahu |
| 2010/0094358 A1 | 4/2010 | Moore |
| 2010/0152787 A1 | 6/2010 | Walsh |
| 2010/0241171 A1 | 9/2010 | Clement |
| 2010/0324488 A1 | 12/2010 | Smith |
| 2011/0034956 A1 | 2/2011 | Mazda |
| 2011/0071569 A1 | 3/2011 | Black |
| 2011/0144687 A1 | 6/2011 | Kleiner |
| 2011/0238118 A1 | 9/2011 | Baccelli |
| 2011/0245857 A1 | 10/2011 | Stan |
| 2011/0270325 A1 | 11/2011 | Keyer |
| 2011/0319940 A1 | 12/2011 | Slivka |
| 2012/0004665 A1 | 1/2012 | Defossez |
| 2012/0022591 A1 | 1/2012 | Baccelli |
| 2012/0022592 A1 | 1/2012 | Belliard |
| 2012/0029566 A1 | 2/2012 | Rezach |
| 2012/0029567 A1 | 2/2012 | Zolotov |
| 2012/0065685 A1 | 3/2012 | Lee |
| 2012/0095417 A1 | 4/2012 | Justis |
| 2012/0108926 A1 | 5/2012 | Kassab |
| 2012/0197298 A1 | 8/2012 | Baccelli |
| 2012/0290010 A1 | 11/2012 | Zamani |
| 2013/0123854 A1 | 5/2013 | Kondrashov |
| 2013/0253516 A1 | 9/2013 | Mackall |
| 2013/0261668 A1 | 10/2013 | Douget |
| 2013/0268004 A1 | 10/2013 | Rathbun |
| 2013/0325070 A1 | 12/2013 | Larroque-Lahitette |

FOREIGN PATENT DOCUMENTS

| | | |
|---|---|---|
| CN | 202342145 U | 7/2012 |
| DE | 4429744 A1 | 2/1996 |
| EP | 0888754 A1 | 1/1991 |
| EP | 0637437 A1 | 2/1995 |
| FR | 2704136 A1 | 10/1994 |
| KR | 20010112139 A | 12/2001 |
| WO | WO-9400062 | 1/1994 |
| WO | WO-9632882 | 10/1996 |
| WO | WO-9848719 | 5/1999 |
| WO | WO-0241796 | 5/2002 |
| WO | WO-03096914 | 11/2003 |
| WO | WO-2005004947 | 1/2005 |
| WO | WO-2006029373 | 3/2006 |
| WO | WO-2006111852 | 10/2006 |
| WO | WO-2008013892 | 1/2008 |

* cited by examiner

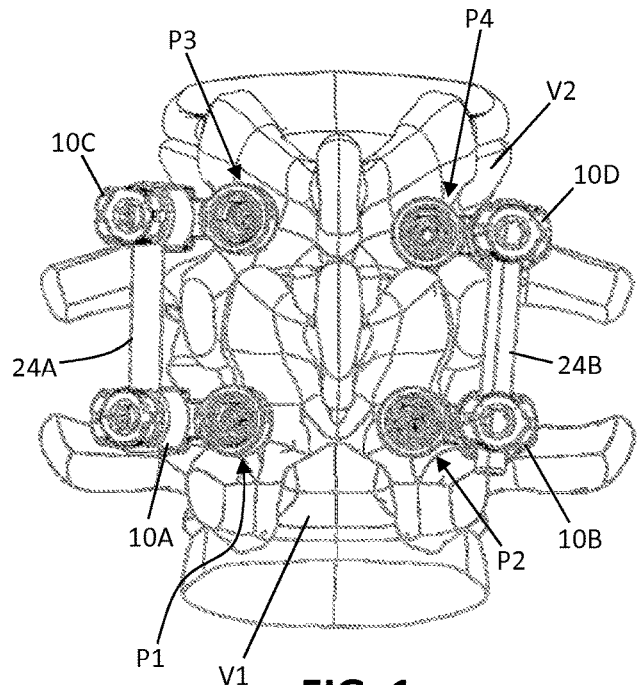
FIG. 1
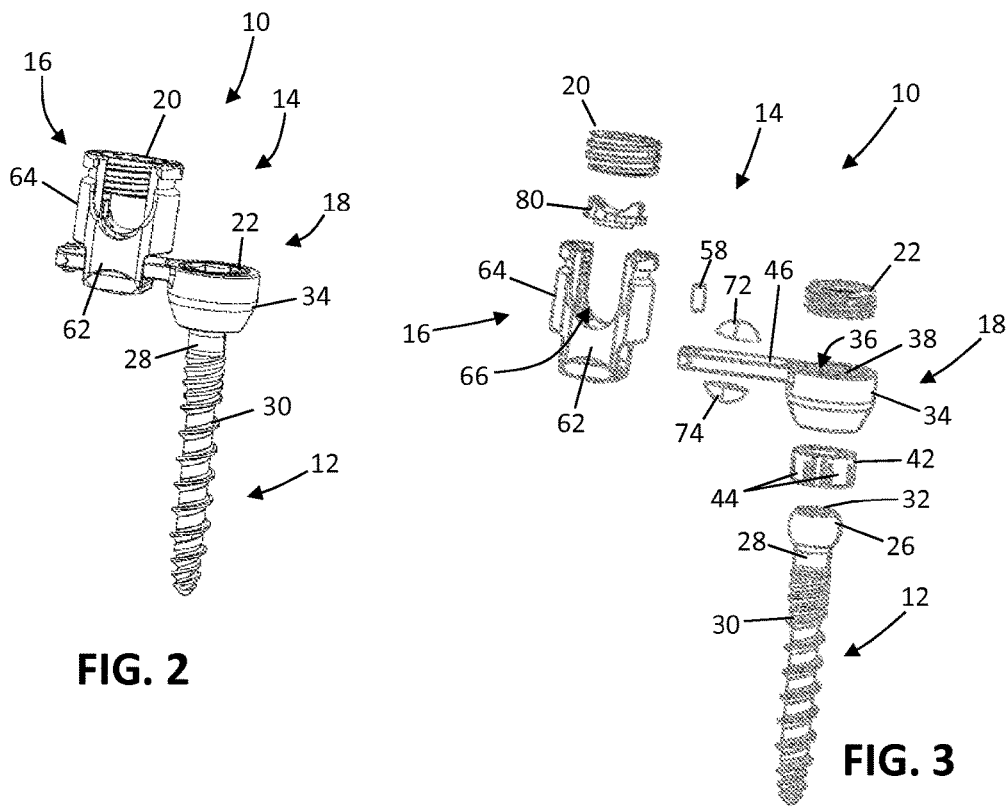
FIG. 2
FIG. 3

BONE ANCHOR WITH OFFSET ROD CONNECTOR

CROSS REFERENCES TO RELATED APPLICATIONS

The present application is a non-provisional application claiming the benefit of priority under 35 U.S.C. §119(e) from U.S. Provisional Application Ser. No. 61/888,480 filed on Oct. 8, 2013, the entire contents of which is hereby incorporated by reference into this disclosure as if set forth fully herein.

FIELD

The present application describes a bone anchor for use as part of a spinal fixation construct.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to treat and correct ailments of the spine.

When conservative efforts fail, treating spinal ailments very often includes a combination of spinal fusion and fixation. Generally, spinal fusion procedures involve removing some or all of an intervertebral disc, and inserting one or more intervertebral implants into the resulting disc space. Introducing the intervertebral implant serves to restore the height between adjacent vertebrae ("disc height") and maintain the height and/or correct vertebral alignment issues until bone growth across the disc space connects the adjacent vertebral bodies. Fusions may be performed across a single level or multiple levels.

Often during spinal fusion procedures a posterior fixation construct is implanted to immobilize the vertebrae to be fused until the fusion is complete. The posterior fixation construct generally includes at least two bone anchors (e.g. pedicle screws, laminar hooks) connected together with a rod. Like the fusion, the fixation construct can be implanted across a single level or across multiple levels, and typically, the fixation system is positioned to at least span each level to be fused. These pedicle screw systems are very effective. However, there can also be challenges associated with them. For example, connecting the rod to each anchor can be difficult since the anchors are not necessarily coplanar. When this happens the rod must be bent to match the position of the anchor, or the entire vertebra must be moved to move the anchor to the rod. There are also instances when the position of the rod and/or the connecting portion of the anchor can obstruct access to spine in close proximity to the anchor.

The devices and methods described in the present application are directed at address these challenges.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein:

FIG. 1 is a top view of a bilateral spinal fixation construct utilizing a quartet of offset bone anchor assemblies, according to an example embodiment;

FIG. 2 is a perspective view of an offset bone anchor assembly, according to one example embodiment;

FIG. 3 is an exploded view of the offset bone anchor assembly of FIG. 2;

Figure 16A:
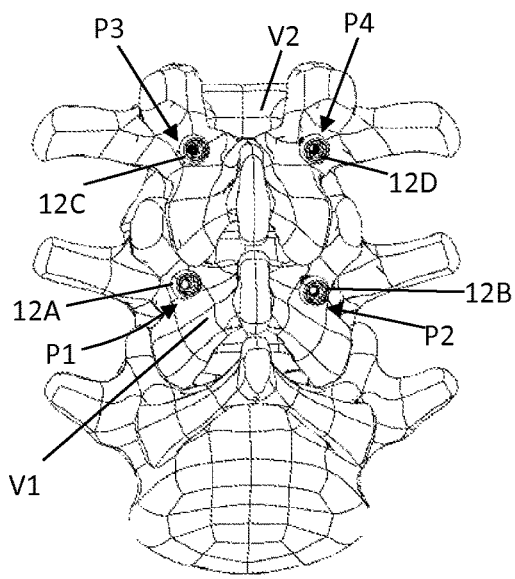
FIGS. 16A-16E are top view illustrations depicting certain steps of an example method for constructing the bilateral fixation construct of FIG. 1.
Figure 17:
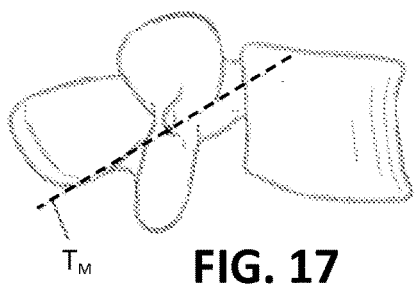
Figure 18:
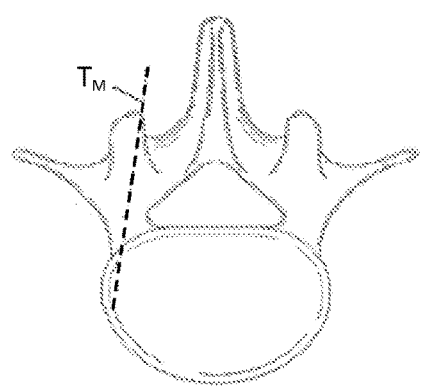
Figure 19:
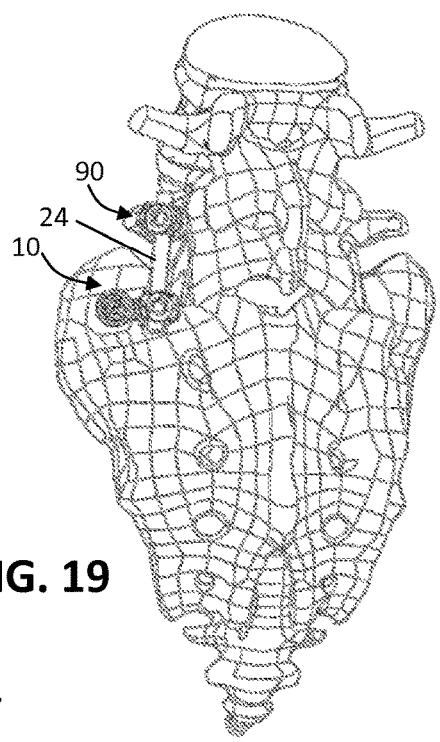

FIGS. 17-18 are lateral and axial views of a vertebra depicting one example of a medialized trajectory for implanting the bone anchors according the example method of FIGS. 16A-1E; and FIG. 19 is a perspective view illustrating one of the offset anchor assemblies of FIG. 2 fixed to the ilium at the caudal end of a fixation construct, the cephalad anchor location being offset medially relative to the ilium anchor locations.

Figure 20:
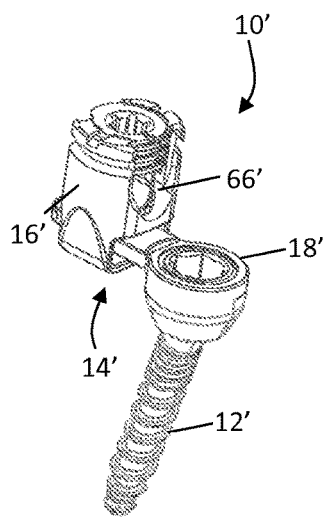
Figure 21:
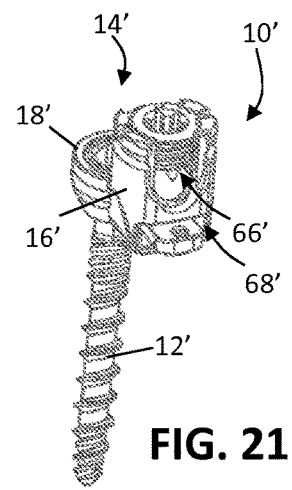
Figure 22:
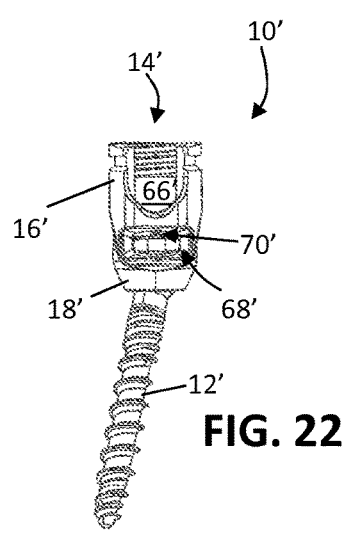

FIGS. 20-21 illustrate perspective views of another example embodiment of an offset bone anchor assembly; and FIG. 22 is a front view of the bone anchor assembly of FIGS. 20-21.

DETAILED DESCRIPTION

Preferred embodiments of devices and techniques for spinal fixation are described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation anchor and methods described herein boast a variety of inventive features and components that warrant patent protection, both individually and in combination.

With reference to FIG. 1, a single level, bilateral spinal fixation construct utilizing a quartet of offset bone anchor assemblies 10 is depicted. More specifically, a first anchor assembly 10A is anchored through the pedicle P1 of lumbar vertebrae V1 and a second anchor assembly 10B is anchored through the contralateral pedicle P2 of V1. A third anchor assembly 10C is anchored through the pedicle P3 of lumbar vertebra V2 adjacent to V1, and a fourth anchor assembly 10D is anchored through pedicle P4 of V2. The anchor assemblies 10A and 10C are connected by a spinal rod 24A and the anchor assemblies 10B and 10D are connected by the spinal rod 24B in order to fix the vertebrae V1 and V2 in position relative to each other. The anchor assemblies 10A-10D include a rod connector that is offset and adjustable with respect to position relative to the shank, in effect, de-coupling the rod position from the shank position. Accordingly, the shank can be placed in the desired location (e.g. pedicle) while the position of the rod connector and rod can be adjusted to accommodate other surgical considerations (e.g. anatomical obstructions, clearance for other implants, grafts, etc. . . . ). By way of example, in the configuration shown, the anchor assemblies 10A-10D are implanted using a medialized trajectory, that is, with a starting point that is more medial to that of a standard pedicle screw starting point (e.g. the starting point may be just medial and inferior to the articulating surface of the superior facet) and angled slightly laterally such that the distal end of the shank lies lateral to the proximal end of the shank at the starting point, and preferably anchored into the cortical bone along the periphery of the vertebral body. The rod position however is offset laterally from the shank which affords a greater opportunity between the shanks for the medial placement of graft material, spinous process plates, or other fusion and fixation elements. In alternative configurations, the offset anchor 10 may be used to achieve a medial offset (e.g. for connecting a construct to the ilium (FIG. 19)) and/or various other anchor types (e.g. standard polyaxial screws, fixed screws, hooks, etc. . . . ) may be used at other anchor locations with one or more offset anchors 10 to achieve the desired fixation construct.

FIGS. 2-13 illustrate an example embodiment of the offset bone anchor assembly 10 that may be used in at least one anchor position along a fixation construct. The anchor assembly 10 includes a shank 12 configured to anchor in bone and a rod connector 14 coupleable to the shank 12 and coupleable to a fixation rod 24. The shank 12 includes a spherical head 26, a neck 28, and a threaded shaft 30. The head 26 includes an engagement recess 32 formed therein that is configured to engage with a suitable driver instrument (not shown). The neck 28 is a generally smooth (e.g. non-threaded) surface extending circumferentially around the bone anchor shank 12 and having a diameter smaller than the diameter of the head 26. The threaded shaft 30 extends distally from the neck 28 and may be any length suitable to achieve the desired bone purchase. As pictured, the threaded shaft 30 employs a triple zoned thread pattern that is designed to maximize purchase with a medialized screw trajectory. The shank 12 may be cannulated to allow for insertion of the shank 12 over a k-wire or other guide instrument, or the shank may be non-cannulated.

Figure 4:
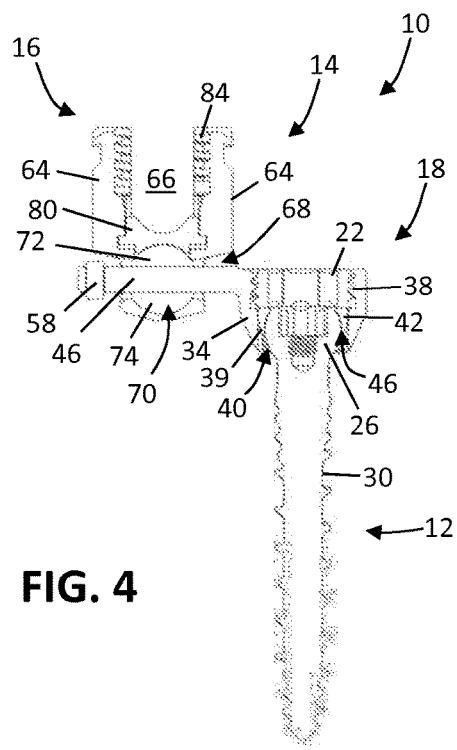
FIG. 4 is a cross-sectional view of the offset bone anchor assembly of FIG. 2.
Figure 5:
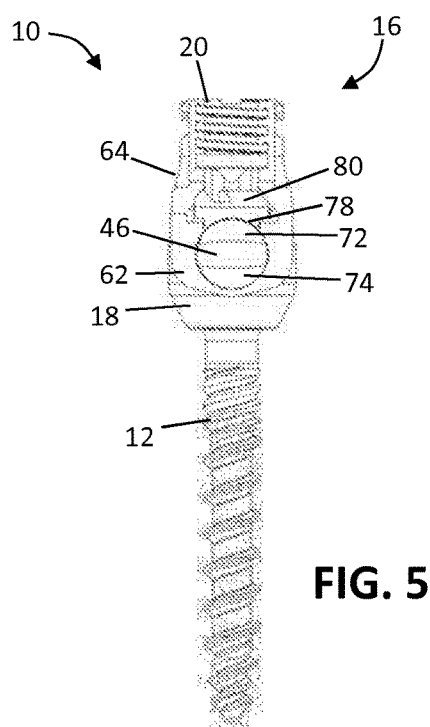
FIG. 5 is a cross-sectional view of the offset bone anchor assembly of FIG. 2, wherein the cross-section extends through a tulip of the bone anchor assembly.
Figure 6:
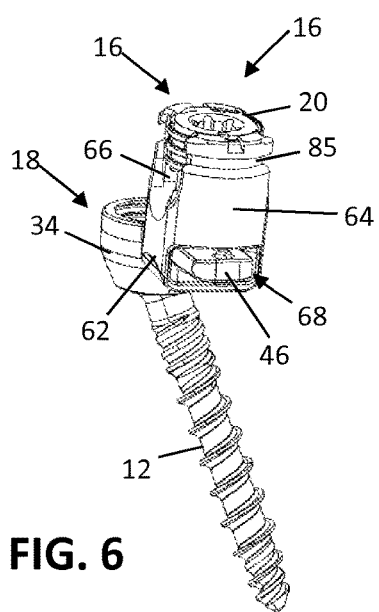
FIG. 6 is another perspective view of the offset bone anchor assembly of FIG. 2.
Figure 7:
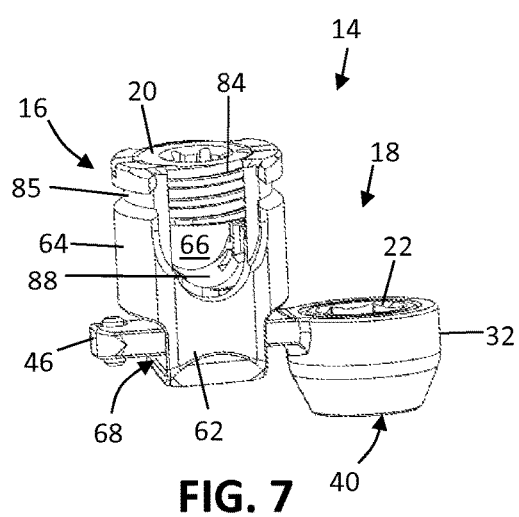
FIG. 7 is a perspective view of a connector of the bone anchor assembly of FIG. 2.

The rod connector 14, shown in FIG. 7, includes a base 18 that couples to the shank 12 and a tulip 16 that receives the rod 24. The base 18 further includes a receptacle 34 with an aperture 36 extending axially therethrough and an arm 46 extending from the receptacle 34 perpendicularly to a longitudinal axis of the aperture 36. The aperture 36 has an upper threaded pocket 38 and a conically tapered lower pocket 40. A cylindrical collet 42 having a plurality of flexible fingers 44 is situated within the lower pocket 40 and a spherical pocket 45 within the collet 42 is configured to receive the spherical head 26 of the shank 12. The anchor locking cap 22 is advancable through the threaded upper pocket 38 into engagement with the collet 42 and forces the collet 42 deeper into the lower pocket 40 such that the flexible fingers 44 are directed inwards as they advance along the conical taper 39. Thus, when the shank head 28 is captured within the spherical pocket 45 of the collet 42 and the anchor locking cap 22 is engaged, the flexible fingers 44 collapse inwards and close about the spherical head 26, locking the connector 14 to the shank 12 and fixing the position of the base 18 relative to the shank. Prior to locking, the spherical head 26 can rotate within the spherical pocket 45 of the collet 42 such that the base 18 is polyaxially coupled to the shank 12. According to one example, in use the shank 12 may be anchored into the vertebra first, free of the connector 14. Thereafter, the receptacle 34 can be advanced onto the shank 12 until the shank head 26 rests in the spherical pocket 45 of the collet 42.

Figure 8:
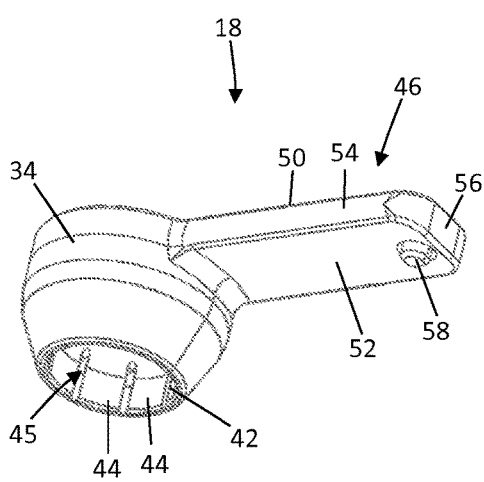
FIG. 8 is a perspective view of a base of the connector of FIG. 7.
Figure 9:
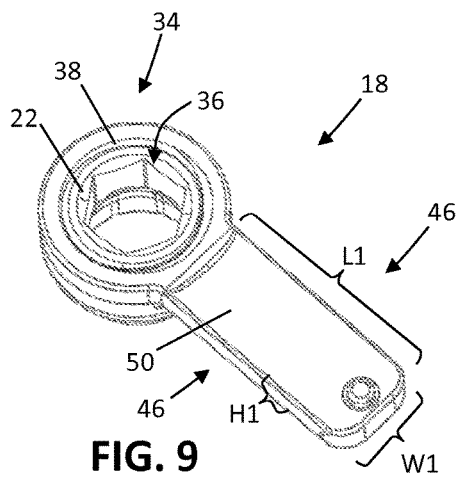
FIG. 9 is another perspective view of a base of the connector of FIG. 7.
Figure 10:
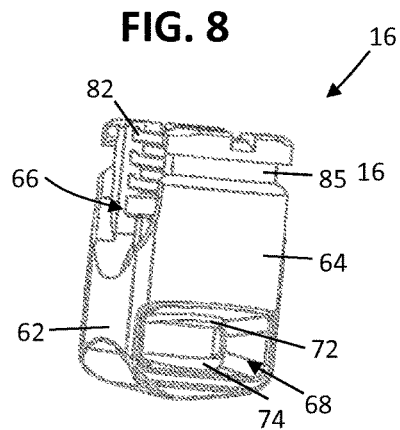
FIG. 10 is a perspective view of a tulip of the connector of FIG. 7.
Figure 11:
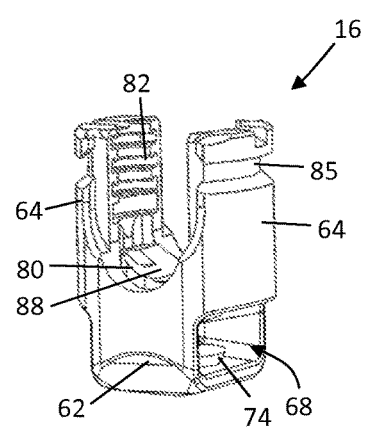
FIG. 11 is another perspective view of the tulip of the connector of FIG. 7.
Figure 12:
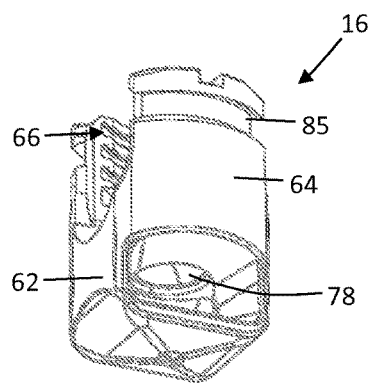
FIG. 12 is another perspective view of the tulip of the connector of FIG. 7 shown without a compressible member that is situated within the tulip.
Figure 13:
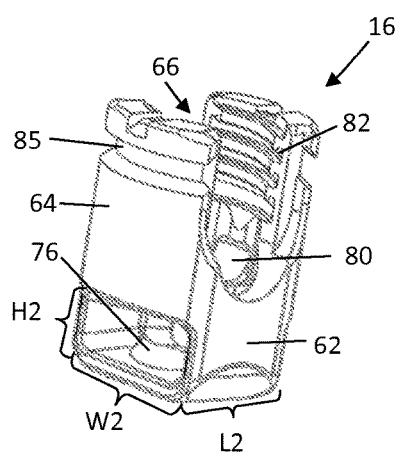
FIG. 13 is another perspective view of the tulip of the connector of FIG. 7 shown without the compressible member.

With reference to FIGS. 8-9, the arm 46 of base 18 has an upper surface 50 and a lower surface 52 which are separated by sidewalls 54 and endwall 56 such that the arm has a length L1 between the endwall 56 and the receptacle 34, a height H1 between the upper surface 50 and lower surface 52, and a width W1 between the sidewalls 54. The tulip 16 slidably and rotatably couples to the arm 46 and a pin 58, which may be press fit, welded, or otherwise securely engaged in a hole 60 adjacent the endwall 56 maintains the tulip 16 on the arm 46 after assembly.

FIGS. 10-13 illustrate the tulip 16. The tulip 16 includes a pedestal 62 and a pair of upstanding arms 64 extending from the pedestal and separated by a rod channel 66. The pedestal 62 defines a passage 68 through which the arm 46 is situated. The passage 68 runs perpendicular to the rod channel 66 such that a rod captured in the tulip will lie transverse to the arm length L1 and offset from the shank 12. A spherical compression element 70 situated within the passage 68 includes an upper compression element 72 and a lower compression element 74. The lower compression element has a spherical lower surface that rests in a spherical cavity 76 in the passage floor and a planar upper surface that contacts the lower surface 52 of the arm 46. The upper compression element 72 has a spherical upper surface that rests in a spherical cavity 78 on the underside of the load ring 80 upon which the rod 24 sits and a planar lower surface that contacts the upper surface 50 of the arm 46. The lower surface of the upper compression element 72 can slide along the upper surface 50 of the arm and the upper surface of the lower compression element 74 can slide along the lower surface 52 of the arm 46 such the compression element 70 can translate along the arm 46 to adjust the position of the tulip along the length of the arm 46 and relative to the shank 12. The tulip 16, via spherical cavity 76 and spherical cavity 78, can also rotate around the spherical compression element 70 such that the tulip 16 can rotate about the arm 46. The passage 68 through pedestal 62 includes a height H2 that is greater than the arm height H1 and a width W2 that is greater than the arm width W1 such that the rotation around the compression element 70 is permitted in all direction to a limited extent. Similarly, the passage has a length L2 that is less than the arm length L1 so that the tulip 16 can translation along the arm 46.

The upstanding arms 64 are equipped with a guide and advancement feature 82, such as by way of example, a helically wound flange feature disposed on the interior face of each arm 64. The guide and advancement feature 82 mates with a complementary guide and advancement feature 84 on the rod locking cap 20 (FIG. 3). The upstanding arms also include an engagement feature 85 that provides an attachment point for coupling the tulip 16 to various instruments that may be used during the procedure (e.g. a rod reduction instrument, compressor, distractor, etc. . . . ). The load ring 80 has a concave, semi-cylindrical upper surface 88 that forms a cradle to receive the spinal rod 24. As the rod locking cap 20 engages the upstanding arms 64 via the complementary guide and advancement features 82, 84, the locking cap forces the rod 24 down into the load ring 80 which in turn presses down against the upper compression element 72. The upper compression element presses down against the arm 46 which loads the lower compression element against the pedestal. Fully engaging the rod locking cap 20 seizes the mechanism and locks the position and orientation of the tulip relative to the arm 46, and thus too, to the shank 12.

Figure 14:
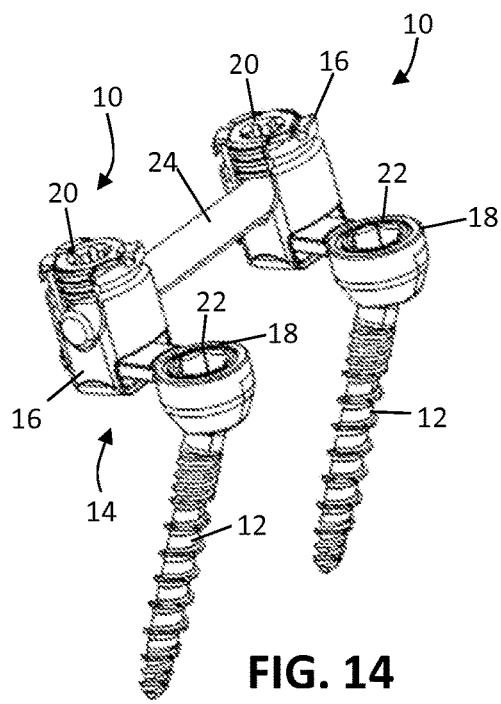
FIG. 14 is a perspective view illustrating two of the offset bone anchor assemblies of FIG. 2 coupled together by a laterally offset spinal rod.
Figure 15:
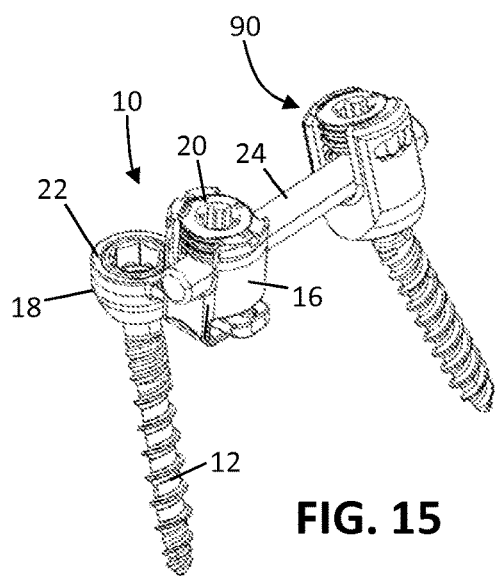
FIG. 15 is a perspective view illustrating one of the offset bone anchor assemblies of FIG. 2 coupled together with a polyaxial screw by a spinal rod medially offset from the offset bone anchor assembly.

With reference to FIG. 14-15, the offset anchor assembly 10 described above can be utilized in any number of ways and configurations when constructing a spinal fixation construct. By way of example, FIG. 14 depicts a pair of offset anchor assemblies 10 used at each end of a single level construct with the tulips 16 offset laterally. As previously noted this configuration may be particularly useful when applied in a medialized posterior fusion surgery wherein anchors are medialized, as will be described below, or by way of another example, for fusion of the posterior elements and spinous process fixation. FIG. 15 depicts a construct in which a single offset anchor assembly 10 is used at the caudal end of a single level construct and the tulip offset medially. A regular polyaxial pedicle screw 90 is used at the caudal end of the construct. This configuration may be useful for example, to fix the cephalad end of the construct to the ilium where the desired anchor location lies more lateral than the spinal levels above it. This is depicted, for example in FIG. 19. Additionally, the offset anchor 10 may be used at any one or more anchor locations of a multilevel construct and offset medially or lateral depending on the goal to be achieved.

Figure 16B:
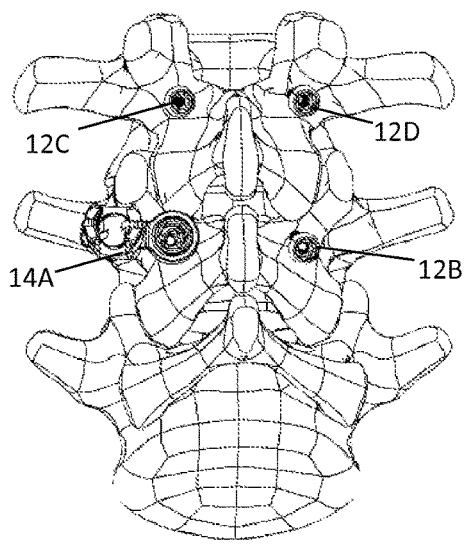
Figure 16C:
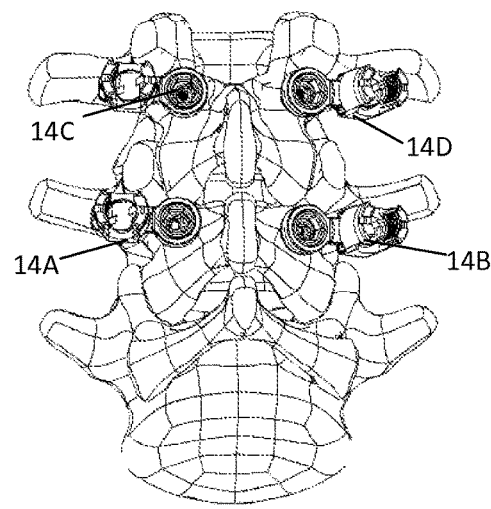
Figure 16D:
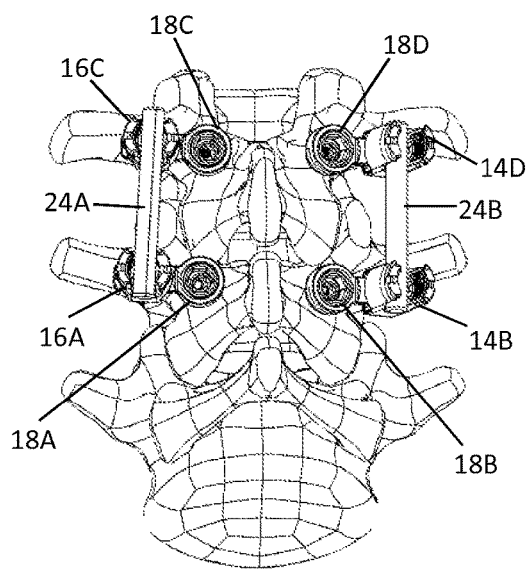
Figure 16E:
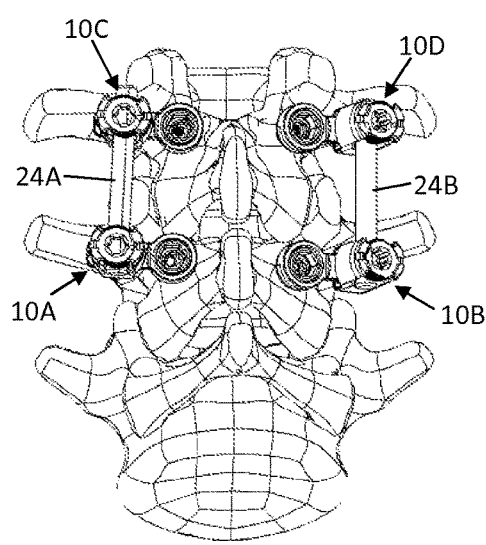

Now with reference to FIGS. 16A-16E, a preferred method for employing anchor assembly 10 with a spinal fixation construct is described. First, after the affected spinal level is identified, a midline incision is made and the necessary anatomy, including pedicles P1 and P2 of vertebrae V1 and pedicles P3 and P4 of vertebra V2, is exposed. A tissue retractor may be employed to maintain access to the exposed spinal anatomy and hold tissue out of the operative corridor. Next, and with reference to FIG. 16A, a shank is anchored into each pedicle. For example, a first shank 12A is anchored through pedicle P1, a second shank 12B is anchored through pedicle P2, a third shank 12C is anchored through pedicle P3, and a fourth shank 12D is anchored through the pedicle P4. The shanks 12A-12D are implanted along a medialized trajectory, which is depicted by way of example as trajectory $T_M$ in FIGS. 17-18. The medialized trajectories between the shanks anchored in the same vertebra (e.g. 12A-12B in V1 and 12C-12D in V2) diverge and may also be directed slightly superiorly. Inserting screws along this trajectory generally allows for placement of a shorter screw shank than those placed along traditional trajectories because the medialized trajectory takes advantage of the anatomical location of cortical bone within the vertebral body. Once the shanks 12A-12D are inserted any therapy to be performed on the spine (e.g. decompression, discectomy, interbody implant insertion, etc. . . . ) may be completed. Then, as illustrated in FIG. 16B, the base 18A of rod connector 14A is coupled to the head of shank 12A with the tulip 16A offset laterally to the shank. The connector may be rotated about the shank head until the desired position is achieved and then the anchor locking cap 22 is engaged to lock the connector. 14A relative to the shank 12A. These steps are repeated for each additional rod connector 14B-14D, as shown in FIG. 16C. Coupling the rod connectors after performing the therapy on the spine allows for more space within the surgical exposure to operate on the spine and perform the desired therapy as there is less hardware present during the procedure. Turning to FIG. 16D, once the connectors 14A-D are coupled to their respective shanks 12A-d, a first rod 24A is inserted into position to connect tulips 16A and 16C and a second rod 24B is inserted into position to connect tulips 16B and 16C. To facilitate rod capture, the tulips 16 can translate along the base arm 46 and/or rotate relative to the arm 46 to adjust the position and orientation of the tulip. With the rods 24A-24B appropriately situated, the rod locking caps 20A-20D are fully engaged in the tulips to complete the construct, as shown in FIG. 16E, arresting any further movement of the tulips and fixing the position of vertebra V1 and Vertebra V2 relative to each other.

FIGS. 20-22 illustrate a second example embodiment of an offset anchor assembly 10' to be utilized at least one anchor location of a spinal fixation construct. The offset connector 10' includes a shank 12' and connector 14' that further includes a tulip 16' and base 18'. The shank 12' and base 18' are identical to the shank 12 and base 18 previously described. The tulip 16' is also identical to the tulip 16, except in that the passage 68' 68 runs parallel to the rod channel 66' such that a rod captured in the tulip 16' will lie generally in line with the arm length. Under typical circumstances in this configuration the offset of the tulip becomes one of a cranial or caudal offset as opposed to the medial or lateral offset provided by anchor assembly 10.

It is further contemplated that the compressible member 70 of anchor assembly 10 or compressible member 70' of anchor assembly 10' may be configured such that when the rod locking cap is fully engaged, the compressible member provides resistance against movement, but does arrest movement entirely. Or alternatively, the compressible member will resist all movement up to a certain force, above which the compressible member will give and some movement will be achieved. In effect, the provides for a semi-rigid connection that provides controlled motion in that tulip (and thus the rod captured within the tulip) has some freedom to translate and/or rotate relative to the arm which can accommodate natural shifting and/or realignment pressure that may occur after the construct is completed. It is believed that this ability to accommodate some degree of controlled movement, particularly with the anchor assembly 10 or 10' positioned at the end of a construct, an especially a long construct, may have beneficial effects in preventing the development of adjacent segment pathology like Proximal Junctional Kyphosis (PJK) which is thought to possibly be caused by excess strain and stress on the proximal instrumented spinal segment which is then at least partially transferred to the bone structures, disc, ligaments and other soft tissues, causing a loss of normal structural integrity and mechanical properties.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

We claim:

1. A spinal anchor, comprising:
    a shank having a threaded region for anchoring in bone, and a spherical head; and
    an offset connector for coupling the shank to a spinal rod offset from an axis of the shank, wherein the offset connector comprises:
        a base, the base having a first end with a receptacle for forming a first lockable polyaxial joint with the spherical head of the shank, the base further including an arm that extends from the receptacle, the arm having a first length, a first height, and a first width; and
        a tulip, the tulip forming a second lockable polyaxial joint translatable along a length of the base and having a rod channel for coupling the tulip to a spinal rod, the tulip further including a passage, the passage having a second length less than the first length, a second height greater than the first height, and a second width greater than the first width, the arm of the base extending through the passage such that the arm can rotate relative to the tulip while extending through the passage, the arm also extending through a compressible member situated within the passage, the compressible member comprising the second polyaxial joint.

2. The spinal anchor of claim 1, wherein the receptacle includes a collet having an interior spherical pocket that receives the spherical head of the shank.

3. The spinal anchor of claim 2, wherein the collet is advanced along a conical taper within the receptacle to collapse the collet around the spherical head of the shank and lock the first polyaxial joint.

4. The spinal anchor of claim 3, wherein a locking cap threadingly engages the receptacle to advance the collet along the conical taper.

5. The bone anchor of claim 1, wherein the compressible member includes a first compressible element having a spherical first upper side and a planar first under side and a second compressible element having a planar second upper side and a spherical second underside, and wherein the arm slidably engages the planar first under surface and the planar second upper surface such that the arm such that the tulip is translatable along the arm.

6. The spinal anchor of claim 5, wherein the spherical first upper surface rests in a first spherical cavity within the tulip and the spherical second under surface rests in a second spherical cavity within the tulip, such that the tulip is rotatable about the compressible member and relative to the base.

7. The spinal anchor of claim 6, wherein the first spherical cavity is formed by the lower surface of a load ring situated in the tulip, the load ring having an upper surface for seating the rod.

8. The spinal anchor of claim 7, wherein forcing a rod against the load ring causes the load ring to load the compressible member and lock the second polyaxial joint.

9. The spinal anchor of claim 8, wherein a locking cap engages with the tulip to force the rod against the load ring.

10. A spinal anchor, comprising:
    a shank having a threaded region for anchoring in bone; and
    an offset connector for coupling the shank to a spinal rod offset from an axis of the shank, wherein the offset connector comprises:
        a base having a first end connectable to the shank and an arm that extends from the first end, the arm having a first length, a first height, and a first width; and
        a tulip having a rod channel for receiving a spinal rod therein, a passage situated below the rod channel, and a compressible element situated in the passage and polyaxially rotatable therein, the passage having a second length less than the first length, a second height greater than the first height, and a second width greater than the first width, the arm of the base extending through the compressible member and the passage, such that the tulip is translatable along the arm and polyaxially rotatable relative to the base.

11. The spinal anchor of claim 10, wherein the compressible member includes a first compressible element having a spherical first upper side and a planar first under side and a second compressible element having a planar second upper side and a spherical second underside, and wherein the arm slidably engages the planar first under surface and the planar second upper surface thereby permitting the translation of the tulip along the arm.

12. The spinal anchor of claim 11, wherein the spherical first upper surface rests in a first spherical cavity within the tulip and the spherical second under surface rests in a second spherical cavity within the tulip.

13. The spinal anchor of claim 12, wherein the first spherical cavity is formed by the lower surface of a load ring situated in the tulip, the load ring having an upper surface for seating the rod.

14. The spinal anchor of claim 13, wherein forcing a rod against the load ring causes the load ring to load the compressible member thereby inhibiting further translation of the tulip along the arm and rotation of the tulip relative to the base.

15. The spinal anchor of claim 14, wherein a locking cap engages with the tulip to force the rod against the load ring.

16. The spinal anchor of claim 10, wherein the shank has a spherical head and the first end of the base includes a receptacle that receives the spherical head of the shank.

17. The spinal anchor of claim 16, wherein the receptacle includes a collet having an interior spherical pocket that receives the spherical head of the shank such that the base is polyaxially rotatable relative to the shank, the receptacle defining a conical taper such that the collet collapses around the spherical head of the shank when the collet is forced down the conical taper thereby inhibiting further rotation of the base relative to the shank.

18. The spinal anchor of claim 17, wherein a locking cap engages the receptacle to advance the collet down the conical taper.

\* \* \* \* \*